(12) United States Patent
Lee et al.

(10) Patent No.: US 8,147,557 B2
(45) Date of Patent: Apr. 3, 2012

(54) MOBILE BEARING INSERT HAVING OFFSET DWELL POINT

(75) Inventors: Jordan S. Lee, Warsaw, IN (US); James M. Rhodes, Warsaw, IN (US); John Francis Lizak, Somerset, MA (US)

(73) Assignee: DePuy Products, Inc., Warsaw, IN (US)

( * ) Notice: Subject to any disclaimer, the term of this patent is extended or adjusted under 35 U.S.C. 154(b) by 665 days.

(21) Appl. No.: 11/694,389

(22) Filed: Mar. 30, 2007

(65) Prior Publication Data

US 2008/0243259 A1 Oct. 2, 2008

Related U.S. Application Data

(60) Provisional application No. 60/909,127, filed on Mar. 30, 2007, provisional application No. 60/909,126, filed on Mar. 30, 2007, provisional application No. 60/909,129, filed on Mar. 30, 2007, provisional application No. 60/909,259, filed on Mar. 30, 2007.

(51) Int. Cl.
*A61F 2/38* (2006.01)
(52) U.S. Cl. ............... 623/20.3; 623/20.33; 623/14.12
(58) Field of Classification Search ............ 623/20.33, 623/20.3
See application file for complete search history.

(56) References Cited

U.S. PATENT DOCUMENTS

| | | |
|---|---|---|
| 3,506,982 A | 4/1970 | Steffee |
| 3,605,123 A | 9/1971 | Hahn |
| 3,855,638 A | 12/1974 | Pilliar |
| 3,906,550 A | 9/1975 | Rostoker et al. |
| 3,953,899 A | 5/1976 | Charnley |
| 4,016,606 A | 4/1977 | Murray et al. |
| 4,205,400 A | 6/1980 | Shen et al. |
| 4,207,627 A | 6/1980 | Cloutier |
| 4,213,816 A | 7/1980 | Morris |
| 4,216,549 A | 8/1980 | Hillberry et al. |
| 4,224,696 A | 9/1980 | Murray et al. |
| 4,224,697 A | 9/1980 | Murray et al. |
| 4,340,978 A | 7/1982 | Buechel et al. |
| 4,454,612 A | 6/1984 | McDaniel et al. |
| 4,470,158 A | 9/1984 | Pappas et al. |
| 4,479,271 A | 10/1984 | Bolesky |
| 4,501,031 A | 2/1985 | McDaniel et al. |
| 4,568,348 A | 2/1986 | Johnson et al. |
| 4,589,883 A | 5/1986 | Kenna |

(Continued)

FOREIGN PATENT DOCUMENTS

BE 1008201 2/1996

(Continued)

OTHER PUBLICATIONS

European Search Report for European Patent Application No. 08251210.4-2310, Jun. 20, 2008, 7 pgs.

(Continued)

*Primary Examiner* — Bruce E Snow
*Assistant Examiner* — Melissa Hoban
(74) *Attorney, Agent, or Firm* — Barnes & Thornburg LLP

(57) ABSTRACT

A mobile tibial assembly includes a tibial tray and a tibial insert configured to move relative to the tibial tray. The tibial insert includes a platform having an upper bearing surface defining a dwell point of the upper bearing surface. The dwell point is spaced-apart from a center of the bearing surface.

17 Claims, 6 Drawing Sheets

U.S. PATENT DOCUMENTS

| | | | |
|---|---|---|---|
| 4,636,219 A | 1/1987 | Pratt et al. |
| 4,718,413 A | 1/1988 | Johnson |
| 4,719,908 A | 1/1988 | Averill et al. |
| 4,728,332 A | 3/1988 | Albrektsson |
| 4,743,261 A | 5/1988 | Epinette |
| 4,795,468 A | 1/1989 | Hodorek et al. |
| 4,911,721 A | 3/1990 | Andergaten |
| 4,936,847 A | 6/1990 | Manginelli |
| 4,944,757 A | 7/1990 | Martinez et al. |
| 4,950,298 A | 8/1990 | Gustilo et al. |
| 4,997,445 A | 3/1991 | Hodorek |
| 5,019,103 A | 5/1991 | Van Zile et al. |
| 5,047,058 A | 9/1991 | Roberts et al. |
| 5,108,452 A | 4/1992 | DeMane et al. |
| 5,152,797 A | 10/1992 | Luckman et al. |
| 5,201,769 A | 4/1993 | Schutzer |
| 5,226,915 A | 7/1993 | Bertin |
| 5,263,987 A | 11/1993 | Shah |
| 5,282,868 A | 2/1994 | Bahler |
| 5,330,532 A | 7/1994 | Ranawat |
| D354,810 S | 1/1995 | Nazre |
| 5,395,401 A | 3/1995 | Bahler |
| D357,534 S | 4/1995 | Hayes |
| D359,557 S | 6/1995 | Hayes |
| 5,458,637 A | 10/1995 | Hayes |
| 5,609,639 A | 3/1997 | Walker |
| 5,609,640 A | 3/1997 | Johnson |
| 5,658,341 A | 8/1997 | Delfosse |
| 5,702,458 A | 12/1997 | Burstein et al. |
| 5,702,459 A | 12/1997 | Hummer et al. |
| 5,716,361 A | 2/1998 | Masini |
| 5,755,801 A | 5/1998 | Walker et al. |
| 5,800,560 A | 9/1998 | Draenert |
| 5,810,827 A | 9/1998 | Haines et al. |
| 5,824,106 A | 10/1998 | Fournol |
| 5,855,296 A | 1/1999 | McCann et al. |
| 5,871,541 A | 2/1999 | Gerber |
| 5,879,354 A | 3/1999 | Haines et al. |
| 5,888,034 A | 3/1999 | Greenberg |
| 5,944,722 A | 8/1999 | Masini |
| 5,947,973 A | 9/1999 | Masini |
| 5,957,926 A | 9/1999 | Masini |
| 5,957,979 A | 9/1999 | Beckman et al. |
| 5,961,523 A | 10/1999 | Masini |
| 5,971,989 A | 10/1999 | Masini |
| 6,004,351 A | 12/1999 | Tomita et al. |
| 6,010,534 A | 1/2000 | O'Neil et al. |
| 6,019,767 A | 2/2000 | Howell |
| 6,039,764 A | 3/2000 | Pottenger et al. |
| 6,056,754 A | 5/2000 | Haines et al. |
| 6,068,633 A | 5/2000 | Masini |
| 6,077,269 A | 6/2000 | Masini |
| 6,102,916 A | 8/2000 | Masini |
| 6,106,529 A | 8/2000 | Techiera |
| 6,123,728 A | 9/2000 | Brosnahan et al. |
| 6,139,581 A | 10/2000 | Engh et al. |
| 6,171,340 B1 | 1/2001 | McDowell |
| 6,187,010 B1 | 2/2001 | Masini |
| 6,197,064 B1 | 3/2001 | Haines et al. |
| 6,214,011 B1 | 4/2001 | Masini |
| 6,254,604 B1 | 7/2001 | Howell |
| 6,254,605 B1 | 7/2001 | Howell |
| 6,296,666 B1 | 10/2001 | Gardner |
| 6,361,564 B1 | 3/2002 | Marceaux et al. |
| 6,419,707 B1 | 7/2002 | Leclercq |
| 6,428,577 B1 | 8/2002 | Evans et al. |
| 6,494,914 B2 | 12/2002 | Brown et al. |
| 6,503,254 B2 | 1/2003 | Masini |
| 6,506,215 B1 | 1/2003 | Letot et al. |
| 6,520,964 B2 | 2/2003 | Tallarida et al. |
| 6,602,292 B2 | 8/2003 | Burkinshaw |
| 6,616,696 B1 | 9/2003 | Merchant |
| 6,660,039 B1 | 12/2003 | Evans et al. |
| 6,702,821 B2 | 3/2004 | Bonutti |
| 6,730,128 B2 | 5/2004 | Burstein |
| 6,770,078 B2 | 8/2004 | Bonutti |
| 6,869,448 B2 | 3/2005 | Tuke et al. |
| 6,916,341 B2 | 7/2005 | Rolston |
| 6,946,001 B2 | 9/2005 | Sanford et al. |
| 7,033,397 B2 | 4/2006 | Webster et al. |
| 7,101,401 B2 | 9/2006 | Brack |
| 7,105,027 B2 | 9/2006 | Lipman et al. |
| 7,115,131 B2 | 10/2006 | Engh et al. |
| 7,708,741 B1 | 5/2010 | Bonutti |
| 7,931,690 B1 | 4/2011 | Bonutti |
| 2001/0037155 A1 | 11/2001 | Merchant |
| 2002/0055784 A1 | 5/2002 | Burstein et al. |
| 2003/0009232 A1 | 1/2003 | Metzger et al. |
| 2003/0028196 A1 | 2/2003 | Bonutti |
| 2003/0033018 A1 | 2/2003 | Merchant |
| 2003/0120346 A1 | 6/2003 | Mercinek et al. |
| 2003/0158606 A1 | 8/2003 | Coon et al. |
| 2003/0181984 A1 | 9/2003 | Abendschein |
| 2003/0187510 A1 | 10/2003 | Hyde |
| 2003/0195633 A1 | 10/2003 | Hyde |
| 2004/0006394 A1 | 1/2004 | Lipman et al. |
| 2004/0039447 A1 | 2/2004 | Simon et al. |
| 2004/0107000 A1* | 6/2004 | Felt et al. ............. 623/20.32 |
| 2004/0143338 A1 | 7/2004 | Burkinshaw et al. |
| 2004/0153066 A1 | 8/2004 | Coon et al. |
| 2004/0153164 A1 | 8/2004 | Sanford et al. |
| 2004/0167630 A1 | 8/2004 | Rolston |
| 2004/0193280 A1* | 9/2004 | Webster et al. ............ 623/20.33 |
| 2004/0254645 A1 | 12/2004 | Arnin et al. |
| 2005/0015153 A1 | 1/2005 | Goble et al. |
| 2005/0027365 A1 | 2/2005 | Burstein et al. |
| 2005/0096747 A1* | 5/2005 | Tuttle et al. ............. 623/20.32 |
| 2005/0119663 A1 | 6/2005 | Keyer et al. |
| 2005/0119664 A1 | 6/2005 | Carignan et al. |
| 2005/0143830 A1 | 6/2005 | Marcinek et al. |
| 2005/0143831 A1 | 6/2005 | Justin et al. |
| 2005/0143833 A1 | 6/2005 | Merchant |
| 2005/0149041 A1 | 7/2005 | McGinley et al. |
| 2005/0171604 A1 | 8/2005 | Michalow |
| 2005/0171612 A1 | 8/2005 | Rolston |
| 2005/0177242 A1 | 8/2005 | Lotke |
| 2005/0197709 A1* | 9/2005 | Schaefer et al. ............ 623/20.3 |
| 2005/0203384 A1 | 9/2005 | Sati et al. |
| 2005/0234465 A1 | 10/2005 | McCombs et al. |
| 2005/0240273 A1 | 10/2005 | Khandkar et al. |
| 2005/0278034 A1 | 12/2005 | Johnson et al. |
| 2006/0004460 A1 | 1/2006 | Engh et al. |
| 2006/0009776 A1 | 1/2006 | Justin et al. |
| 2006/0009854 A1 | 1/2006 | Justin et al. |
| 2006/0009855 A1 | 1/2006 | Goble et al. |
| 2006/0030855 A1 | 2/2006 | Haines |
| 2006/0030945 A1 | 2/2006 | Wright |
| 2006/0085072 A1 | 4/2006 | Funk et al. |
| 2006/0089720 A1 | 4/2006 | Schneier |
| 2006/0122616 A1 | 6/2006 | Bennett et al. |
| 2006/0129246 A1 | 6/2006 | Steffensmeier |
| 2006/0190086 A1 | 8/2006 | Clemow et al. |
| 2006/0195195 A1 | 8/2006 | Burstein et al. |
| 2006/0195196 A1 | 8/2006 | Pendleton et al. |
| 2006/0235537 A1 | 10/2006 | Kuczynski et al. |
| 2006/0265079 A1 | 11/2006 | D'Alessio |
| 2007/0010890 A1 | 1/2007 | Collazo |
| 2007/0100459 A1 | 5/2007 | Rhodes |
| 2007/0100460 A1 | 5/2007 | Rhodes |
| 2008/0033567 A1 | 2/2008 | Stchur |
| 2008/0086210 A1 | 4/2008 | Fox |

FOREIGN PATENT DOCUMENTS

| | | |
|---|---|---|
| DE | 10012060 | 9/2001 |
| DE | 10053623 | 5/2002 |
| EP | 0135319 A2 | 3/1985 |
| EP | 0183670 | 6/1986 |
| EP | 0327387 A2 | 8/1989 |
| EP | 0328463 A1 | 8/1989 |
| EP | 0874596 A1 | 11/1998 |
| EP | 0709075 B1 | 2/2001 |
| EP | 1327424 | 7/2003 |
| EP | 1329205 A1 | 7/2003 |
| EP | 1374782 A2 | 1/2004 |
| EP | 1442728 A2 | 2/2004 |
| EP | 1442726 | 8/2004 |
| EP | 1550418 | 7/2005 |

| | | |
|---|---|---|
| EP | 1584309 | 10/2005 |
| EP | 1669034 A1 | 6/2006 |
| EP | 1702590 A2 | 9/2006 |
| EP | 1741412 | 1/2007 |
| EP | 1557144 A1 | 7/2007 |
| FR | 2663536 | 12/1991 |
| FR | 2702369 | 9/1994 |
| FR | 2721820 | 1/1996 |
| FR | 2885516 | 11/2006 |
| GB | 2355935 | 5/2001 |
| JP | 2002272756 | 9/2002 |
| WO | 9110412 A1 | 7/1991 |
| WO | 9524874 A1 | 9/1995 |
| WO | 9716129 A1 | 5/1997 |
| WO | 0013616 A1 | 3/2000 |
| WO | 0170143 A1 | 9/2001 |
| WO | 0209623 | 2/2002 |
| WO | 03068119 A2 | 8/2003 |
| WO | 2004001569 A2 | 12/2003 |
| WO | 2005009298 A1 | 2/2005 |
| WO | 2005025451 A2 | 3/2005 |
| WO | 2005037065 A2 | 4/2005 |
| WO | 2005044150 A1 | 5/2005 |
| WO | 2005069957 A2 | 8/2005 |
| WO | 2006074503 A1 | 7/2006 |
| WO | 2006078511 A1 | 7/2006 |
| WO | 2006078528 A2 | 7/2006 |
| WO | 2006078864 A1 | 7/2006 |
| WO | 2006106419 A2 | 10/2006 |
| WO | 2006112911 A2 | 10/2006 |

OTHER PUBLICATIONS

European Search Report for European Patent Application No. 08251213.8-2310, Jul. 9, 2008, 7 pgs.

"The Oxford Partial Knee", Biomet Patents and Caregivers-Joint Replacement, www.biomet.com/patents/oxford.cfm, Biomet, Inc. 2008, 3 pages.

"Preservation Uni-compartmental Knee", DePuy Orthopaedics, Inc. 2002, 31 pages.

European Search Report for European Patent Application No. 08251211.2-2310, Jul. 21, 2008, 7 pgs.

European Search Report for European Patent Application No. 08251209.6-2310, Jul. 9, 2008, 7 pgs.

European Search Report for European Patent Application No. 08251212.0-2310, Jul. 21, 2008, 7 pgs.

European search report; European Patent Application No. 10189885.6-2310; Mar. 18, 2011; 7 pages.

Extended European Search Report for European Patent Application No. 10189881.5-2310, Feb. 17, 2011, 6 pgs.

Chinese First Office Action, Chinese Patent Application No. 200810125845.8, Aug. 24, 2011, 7 pages.

Chinese First Office Action, Chinese Patent Application No. 200810128765.8, Aug. 15, 2011, 8 pages.

\* cited by examiner

MOBILE BEARING INSERT HAVING OFFSET DWELL POINT

CROSS-REFERENCE TO RELATED APPLICATIONS

Cross-reference is made to U.S. Provisional Patent Application Ser. No. 60/909,127 entitled "MOBILE BEARING ASSEMBLY," which was filed on Mar. 30, 2007 by Jordan S. Lee et al. (265280-201718), to U.S. Provisional Patent Application Ser. No. 60/909,126 entitled "MOBILE BEARING ASSEMBLY HAVING A CLOSED TRACK," which was filed on Mar. 30, 2007 by Joseph G. Wyss et al. (265280-200461), to U.S. Provisional Patent Application Ser. No. 60/909,129 entitled "MOBILE BEARING ASSEMBLY HAVING MULTIPLE ARTICULATION INTERFACES," which was filed on Mar. 30, 2007 by Jordan S. Lee et al. (265280-200460), and to U.S. Provisional Patent Application Ser. No. 60/909,259 entitled "MOBILE BEARING ASSEMBLY HAVING A NON-PLANAR INTERFACE," which was filed on Mar. 30, 2007 by Jordan S. Lee et al. (265280-200459), the entirely entirety of which is expressly incorporated herein by reference.

FIELD OF THE DISCLOSURE

The present disclosure relates generally to orthopedic prostheses, and particularly to tibial assemblies including a tibial tray and a tibial insert.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis, for example. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements in which a separate unicompartmental tibial insert is used to replace each of the medial and lateral condyles of the patient. A single, total femoral component or two partial femoral components may be used to cooperate with the two unicompartment inserts.

In addition, in some knee replacement procedures, a total knee tibial tray may be used with a unicompartmental tibial insert. For example, a total knee tibial tray may be used with a single unicompartmental tibial insert to replace either the medial or lateral condyle of the patient's knee. Alternatively, a total knee tibial tray may be used with two unicompartmental tibial inserts, each replacing one of the medial and lateral condyles of the patient's knee. In such applications, the medial and lateral unicompartmental tibial inserts may have different characteristics and be selected based on the orthopedic considerations associated with the respective condyle of the patient's knee.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery.

The tibial assembly of a unicompartmental knee prosthesis typically includes a tibial tray configured to be coupled to the patient's tibia and a polymer tibial insert positioned on the tibial tray. As discussed above, the tibial tray may be a total or unicompartmental tibial tray. The tibial insert includes an upper bearing surface configured to engage a corresponding articulating condylar surface of a femoral component coupled to the patient's femur. A mobile tibial assembly generally refers to a tibial assembly in which the tibial insert is movable relative to the tibial tray. In other words, the tibial insert may rotate relative to the tray and/or the tibial insert may move medially, laterally, anteriorly, and/or posteriorly relative to the tibial tray. This motion of the tibial insert relative to the tray may be constrained in any number of ways in order to limit the type of motion of the tibial insert. For example, the tibial insert may be limited to anterior/posterior motion relative to the tibial tray and/or rotation of the tibial insert may be limited to something less than 360 degrees of rotation. A fixed tibial assembly generally refers to a tibial assembly in which the tibial insert is not movable relative to the tibial tray and generally remains in a fixed location thereon. Surgeons may choose between fixed and mobile tibial assemblies depending upon the particular needs of the patient.

Furthermore, knee anatomy differs from patient to patient such that the components of knee prostheses (i.e., a tibial tray, a tibial insert, and a femoral component) may be difficult to align with each other in order to maintain optimal positioning of each component relative to each other component as well as to maintain optimal positioning of each component relative to the patient's bone. However, due to the patient's anatomy and/or activity needs, the femur and tibia of the patient may not be so aligned. In such instances, either optimal positioning of the components relative to each other or relative to the patient's bone must be sacrificed.

SUMMARY

According to one aspect of the present disclosure, a mobile tibial assembly includes a tibial tray and a tibial insert. The tibial tray is configured to be coupled to a surgically-prepared surface of the proximal end of a tibia. The tibial tray includes a platform having an upper surface and a channel formed in the upper surface to define spaced-apart first and second side walls and a bottom surface therebetween. The tibial insert includes a platform and a stem extending downwardly from the platform and received within the channel of the tibial tray. The platform of the tibial insert includes (i) a bottom surface configured to engage the upper surface of the platform of the tibial tray and (ii) an upper bearing surface defining a dwell point. Illustratively, the dwell point of the tibial insert is spaced-apart from a midpoint of the width of the bottom surface of the channel in the medial/lateral direction.

The dwell point may be laterally spaced 2-8 mm apart from the midpoint of the width of the bottom surface of the channel and more particularly may be laterally spaced 3-6 mm apart from the midpoint of the width of the bottom surface of the channel.

The illustrative tibial insert may be a unicompartmental tibial insert.

The stem of the tibial insert may be generally circular, square, or hexagonal when viewed in a bottom plan view. The hexagonally-shaped stem may be oriented in six different positions within the channel of the tibial tray. For example, the tibial insert may be oriented in a first position relative to the tibial tray such that a first side wall of the stem of the tibial insert is engaged with the first side wall of the channel and a second side wall of the stem of the tibial insert is engage with the second side wall of the channel. Further, the tibial insert may be oriented in a second position relative to the tibial tray such that a third side wall of the stem of the tibial insert is engaged with the first side wall of the channel and a fourth side wall of the stem of the tibial insert is engaged with the second side wall of the channel. The tibial insert may further be oriented in a third position relative to the tibial tray such that a fifth side wall of the stem of the tibial insert is engaged with the first side wall of the channel and a sixth side wall of the stem of the tibial insert is engaged with the second side wall of the channel.

Illustratively, the square-shaped stem of the tibial insert may include four curved side walls and may be configured to rotate relative to the tibial tray approximately 20 degrees.

The illustrative channel of the tibial tray may be configured to extend from an anterior end of the platform of the tibial tray to a posterior end of the platform of the tibial tray.

According to another aspect of the present disclosure, a mobile tibial assembly includes a tibial tray configured to be coupled to a surgically-prepared surface of the proximal end of a patient's tibia and a tibial insert. The tibial tray includes a platform including an upper surface. The tibial insert includes a platform having (i) a bottom surface positioned on the upper surface of the tibial tray and (ii) an upper bearing surface. The dwell point of the upper bearing surface is spaced-apart 2-8 mm from an axis of rotation about which the tibial insert rotates relative to the tibial tray when the tibial insert is positioned on the tibial tray.

Illustratively, tibial insert may be configured to rotate relative to the tibial tray approximately 360 degrees about the axis of rotation or may be alternatively configured to rotate relative to the tibial tray approximately 20 degrees about the axis of rotation.

The platform of the tibial insert may be generally circular in shape when viewed in a bottom plan view.

According to still another aspect of the present disclosure, an orthopedic implant includes a tibial insert having a platform defining a generally circular shape when viewed in plan view. The platform includes an upper bearing surface and the dwell point of the upper bearing surface is spaced-apart 2-8 mm from the center of the upper bearing surface.

Illustratively, in a particular embodiment, the dwell point of the upper bearing surface may be spaced-apart 3-6 mm from the center of the upper bearing surface.

Further illustratively, the tibial insert may be a unicompartmental tibial insert.

According to yet another aspect of the present disclosure, a method of implanting a tibial assembly includes securing a tibial tray to a surgically-prepared surface of the proximal end of a tibia and placing a stem of a tibial insert within a recess of the tibial tray in order to orient a dwell point of the tibial insert in one of at least four positions. Each of the at least four positions of the dwell point is spaced-apart from a center of the recess of the tibial tray.

According to still another aspect of the present disclosure, a method of making a tibial insert includes determining a center of a bearing surface of the tibial insert when the tibial insert is viewed in a plan view, determining an offset location of the bearing surface to locate the dwell point of the bearing surface. The offset location is laterally spaced-apart from the center of the bearing surface. Further, tibial insert is fabricated such that the dwell point of the bearing surface is located at the offset location. The offset location may be laterally spaced 2-8 mm apart from the center of the bearing surface, or in particular embodiments, may be laterally spaced 3-6 mm apart from the center of the bearing surface.

BRIEF DESCRIPTION OF THE DRAWINGS

The detailed description particularly refers to the accompanying figures in which.

DETAILED DESCRIPTION OF THE DRAWINGS

Figure 1:
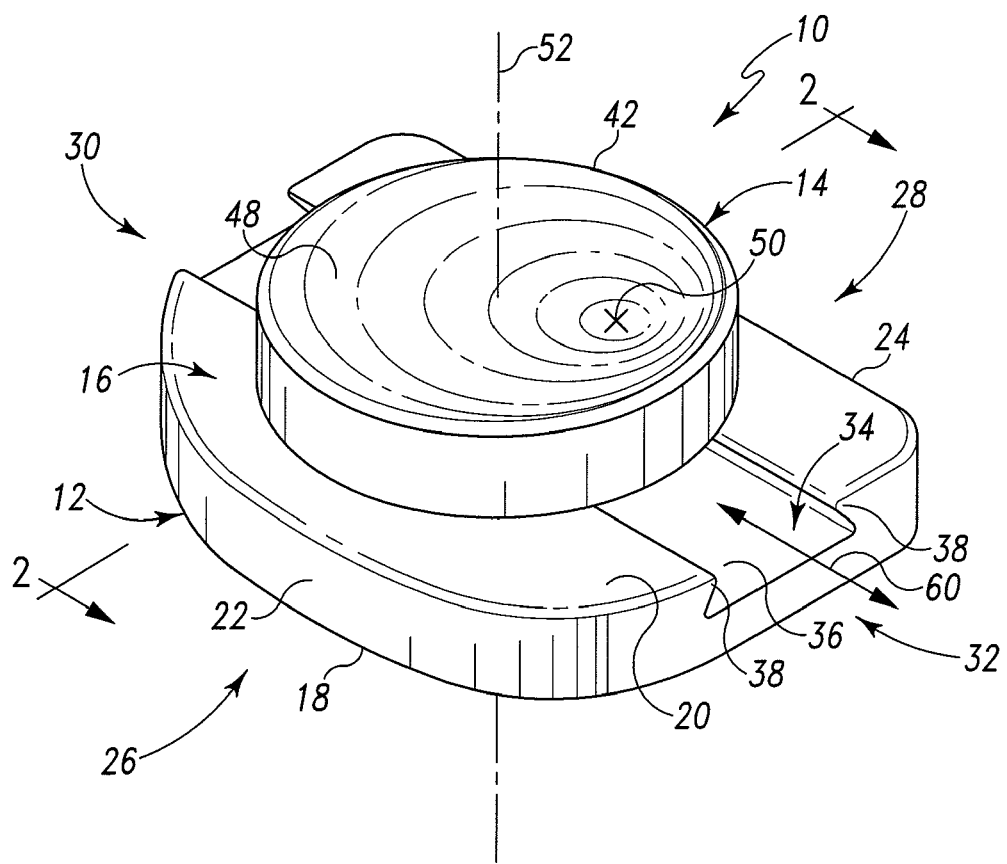
FIG. 1 is a perspective view of a unicompartmental mobile tibial assembly.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

A tibial assembly 10 includes a tibial tray 12 to be coupled to a surgically-prepared surface of the proximal end of a patient's tibia (not shown) and a bearing, or tibial insert 14, provided for use with the tray 12. The tibial insert 14 and other tibial inserts described herein are illustratively formed from a polymer material, but may be formed from other materials, such as a ceramic material, a metallic material, a bio-engineered material, or the like, in other embodiments. Similarly, the tibial tray 12 and other tibial trays described herein, are illustratively formed from a metallic material, but may be formed from other materials, such as a ceramic material, a polymer material, a bio-engineered material, or the like; in other embodiments.

Illustratively, the assembly 10 is a unicompartmental assembly intended to replace only one of the two natural bearing surfaces of a tibia, for example. As such, the tibial assembly 10 may be used by a surgeon or other technician during a unicompartmental knee arthroplasty (UKA). Illustratively, the assembly 10 as well as other tibial assemblies disclosed herein are suitable for use or implantation by surgeons adopting either conventional or minimally invasive surgical methods of performing UKA. Further, although the tibial assembly 10 is a unicompartmental tibial assembly, it is within the scope of this disclosure that the various features associated with the tibial assembly 10, as well as other tibial assemblies discussed herein, may also be associated with tibial assemblies typically used during total knee arthroplasty (TKA) to replace both of the natural bearing surfaces of the tibia. Further, although the features of the tibial assemblies are described in reference to an orthopedic knee implant, it should be appreciated that such features are applicable to other types of orthopedic implants including, but not limited to, hip implants, shoulder implants, elbow implants, spine implants, finger implants, toe implants, wrist implants, and ankle implants.

Figure 2:
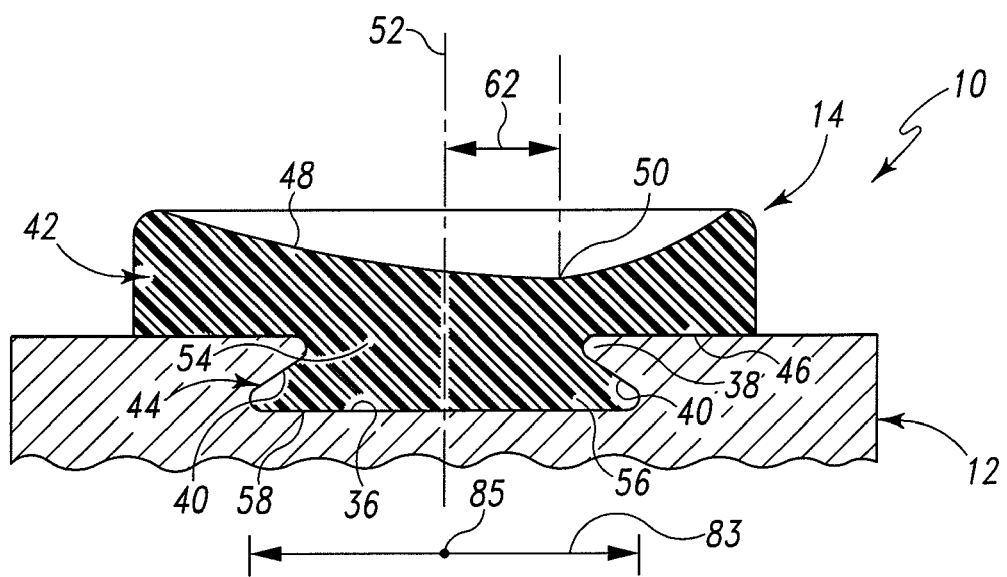
FIG. 2 is a sectional view of the tibial assembly of FIG. 1.
Figure 3:
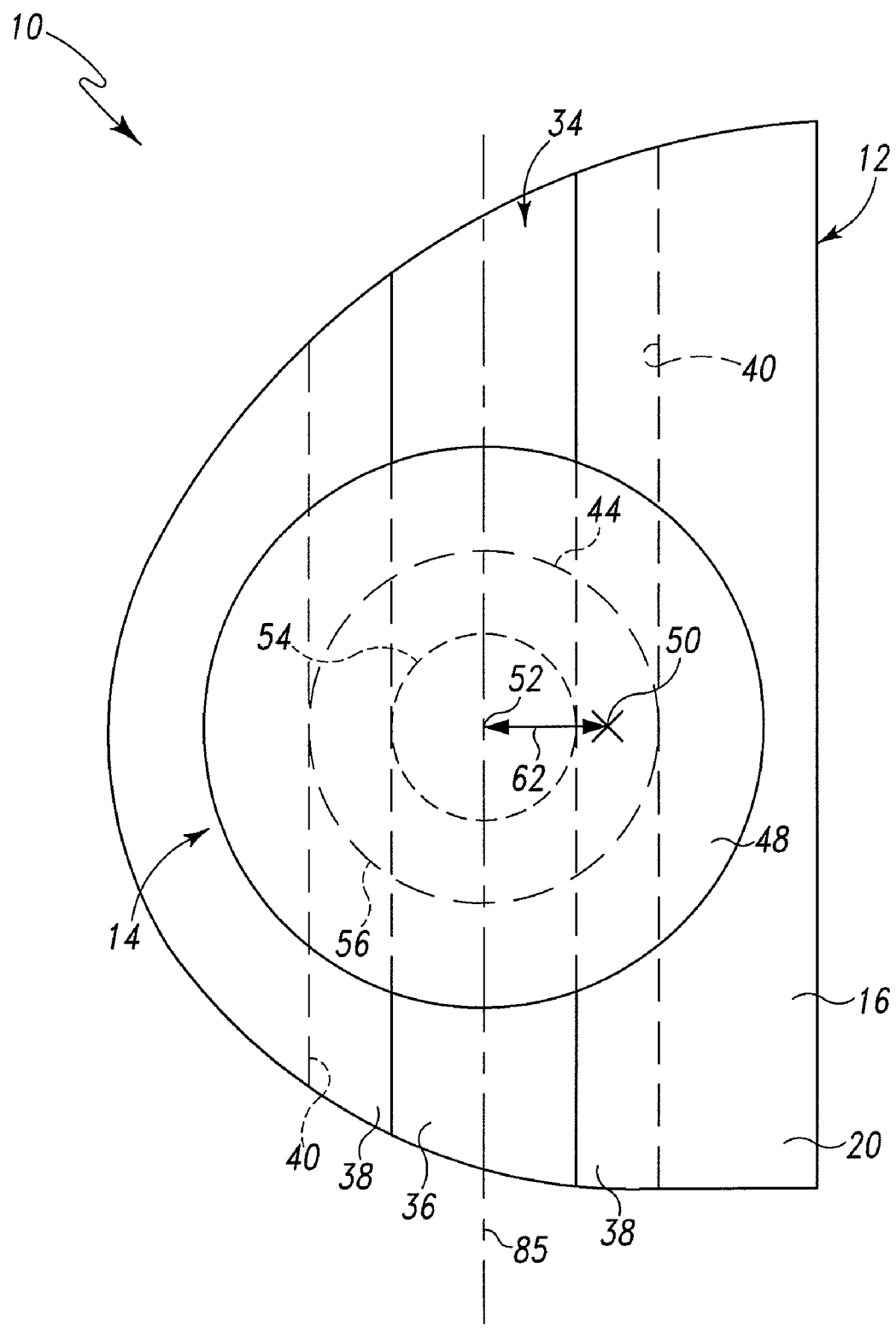
FIG. 3 is a top view of the tibial assembly of FIGS. 1 and 2 showing the dwell point spaced-apart from (i) an axis of rotation of the tibial insert as well as (ii) a centerline along a channel formed in the tibial tray.

Looking now to FIGS. 1-3, the tibial tray 12 includes a platform 16 and, in some embodiments, an anchor component (e.g., a stem or keel, not shown) extending downwardly from the platform 16. During UKA, for example, the stem or keel of the tray 12 is secured to the patient's tibia such that a bottom surface 18 of the platform 16 rests upon a surgically-prepared surface of the tibia. The platform 16 further includes an upper surface 20 and is generally "D-shaped" when viewed in a plan view to define a curved, outer or outboard surface 22 and a generally straight inner or inboard surface 24. However, in other embodiments, the platform 20 may have other configurations based on, for example, the particular joint with which the assembly 10 is used. Illustratively, the outboard surface 22 defines an outboard side 26 of the tibial tray 12 while the inboard surface 24 defines an inboard side 28 such that the tray 12 is further oriented to define a front, or anterior, side 30 and a rear, or posterior, side 32. It should be appreciated that the illustrative tibial assembly 10 is but one embodiment of a tibial assembly and that the features and components of the tibial assembly 10 may be used with a tibial assembly configured to replace the medial and/or lateral condyle of a patient's right tibia, as well as, the medial and/or lateral condyle of the patient's left tibia.

The tibial tray 12 further includes a channel 34 formed in the upper surface 20 of the platform 16 and extending from the anterior side 30 to the posterior side 32 of the platform 16, as shown in FIG. 1. Illustratively, the channel 34 is defined by a bottom surface 36 and medial and lateral rims or overhang portions 38 of the platform 16 which create undercut portions 40 of the channel 34. The channel 34 is defined in the upper surface 20 of the platform 16 in a generally anterior-posterior direction. However, in other embodiments, the channel 34 may be defined in the upper surface 20 of the platform 16 in a generally medial-lateral direction, or some combination of a generally anterior-posterior direction and a generally medial-lateral direction (i.e., a generally diagonal direction). Additionally, although the illustrative channel is substantially straight, the tibial tray 12 may include a channel having other configurations in other embodiments. For example, a curved channel may be used in some embodiments. As is discussed in greater detail below, the channel 34 provides for guided movement of the tibial insert 14 in the anterior and posterior directions.

Similar to the tibial tray 12, the tibial insert 14 includes a platform 42 and a stem 44 extending downwardly from a bottom surface 46 of the platform 42. While the stem 44 and the platform 42 of the insert 14 are coupled to each other to create a unitary insert 14, it is within the scope of this disclosure to provide a modular insert having separate platform and stem components which are coupled together. The illustrative platform 42 of the tibial insert 14 is generally circular when viewed in a plan view, but may define other shapes as well. The platform 42 further includes an upper bearing surface 48 configured to cooperate with a corresponding condylar surface of either a femoral component (not shown) coupled to the patient's femur or a the patient's natural femur itself. Accordingly, the bearing surface 48 provides a surface upon which a prosthetic or natural femoral condyle articulates. Further, as shown in FIG. 2, the bearing surface 48 defines a dwell point 50. As is conventionally known by those skilled in the art and defined herein, a "dwell point" of a given bearing surface is the lowest point of the bearing surface relative to the tray's bottom surface 18. As is discussed in greater detail below, the dwell point 50 of the insert 14 is spaced-apart, or offset, from an axis of rotation 52 about which the insert 14 rotates when coupled with the tray 12. Looking again to FIG. 2, the illustrative stem 44 of the insert 14 includes a narrowed, neck portion 54 and a wider, base portion 56 coupled to the neck portion 54. Illustratively, a bottom surface 58 of the base portion 56 is circular when viewed in plan, as shown in FIG. 3.

In use, the stem 44 of the insert 14 is received within the channel 34 of the tray 12 such that the bottom surface 46 of the platform 44 of the insert 14 is adjacent to and rests on the upper surface 20 of the platform 16 of the tray 12, as shown in FIG. 1. The narrow neck portion 54 of the insert 14 is received between the overhang portions 38 of the tray 12 in order to prevent lift-off of the insert 14, or upward movement of the insert 14, relative to the tray 12. Accordingly, the insert 14 is able to move anteriorly and posteriorly, as shown by arrow 60, within the channel 34 of the tray 12. Further, the insert 14 is able to rotate relative to the tray 12 about the axis of rotation 52 when the insert 14 is positioned on the tray 12. Illustratively, the insert 14 is able to rotate, generally unimpeded, through 360 degrees of rotation. However, it is within the scope of this disclosure to provide an insert able to rotate about an axis through only a limited range of motion.

As discussed previously, the dwell point 50 of the insert 14 is spaced-apart a distance 62 from the axis of rotation 52 of the insert 14. As shown in FIG. 2, the distance 62 between the axis of rotation 52 of the insert 14 and the dwell point 50 is measured using a straight line parallel to the bottom surface 46 of the insert 14 between the axis of rotation 52 and the dwell point 50. The dwell point 50 is offset from the axis of rotation 52 in a medial, lateral, anterior, or posterior direction, or some combination thereof. Another way to define the distance 62 is that distance between the axis of rotation 52 and an imaginary line through the dwell point 50 which is also perpendicular to the bottom surface 46 of the insert 14. In other words, the distance 62 is not measured along the arc length of the bearing surface 48 of the insert 14. Illustratively, the dwell point 50 of the insert 14 may be spaced approximately greater than 1 mm away from the axis of rotation. In a certain illustrative embodiment, the dwell point 50 is spaced approximately greater than 2 mm away from the axis of rotation while in another embodiment the dwell point 50 is spaced approximately greater than 3 mm way from the axis of rotation. In a more specific embodiment, the dwell point 50 is spaced approximately 2-8 mm away from the axis of rotation 52. Furthermore, in one exemplary embodiment, the dwell point 50 of the insert 14 is spaced approximately 3-6 mm from the axis of rotation 52. It should be appreciated that the amount of offset of the dwell point 50 may be based on or otherwise related to the size of the particular tibial insert 14. For example, the spacing between the dwell point 50 and the axis of rotation of the tibial insert 14 may be proportional to the size of the tibial insert 14 (i.e., the offset increases as the size of the insert 14 increases). For example, in one embodiment, the dwell point 50 is spaced from the axis of rotation of the tibial insert 14 a distance approximately equal to 13%-20% of the medial-lateral width of the tibial insert 14. In one particular embodiment, the dwell point 50 is spaced from the axis of rotation of the tibial insert 14 a distance approximately equal to 15%±0.5% of the medial-lateral width of the tibial insert 14.

Illustratively, the axis of rotation 52 of the insert 14 is generally located at the center of the insert 14. In other words, as noted above, the platform 16 of the insert 14 is generally circular when viewed in plan and the stem 44 of the insert 14 is also generally circular when viewed in plan. The axis of rotation 52 illustratively extends through the center of both the circular platform 16 and the circular stem 44. Illustratively, therefore, the dwell point 50 of the insert 14 is spaced-apart from the center of the platform 16 and stem 44 of the insert 14.

Although the platform 16 and the stem 44 of the insert 14 are circular in shape, it is within the scope of this disclosure to include a tibial insert having a platform and/or stem which are not circular in shape. The center of the bearing surface of such non-circular platforms and/or stems is the centerpoint of such platforms and/or stems (when viewed in plan view) which may be arithmetically determined. The dwell point of the non-circular platforms is generally laterally offset from such a centerpoint. It is also within the scope of this disclosure for the insert 14 to rotate about an axis that is not necessarily located at the center of the platform and/or stem of the insert.

Further illustratively, as shown in FIG. 3, the dwell point 50 of the insert 14 is laterally spaced-apart the distance 62 from a midpoint 85 of the width 83 (as shown in FIG. 2) of the bottom surface 36 of the channel 34. In other words, as viewed in the plan view of FIG. 3, the dwell point 50 is offset in the generally medial/lateral direction from a centerline 85 longitudinally dividing the channel 34 into two generally equal halves. Accordingly, the dwell point 50 of the illustrative tibial insert 14 is spaced-apart from the axis of rotation 52, from the center of the bearing surface 48, and from the midpoint of the width (or centerline) of the bottom surface 36 of the channel 34.

The offset dwell point 50 operates to allow a femoral component to be more desirably positioned relative to the tibial insert to accommodate a particular patient's individual anatomy or activity needs, for example. In general, the knee anatomy differs from patient to patient such that the components of a knee prosthesis, including a tibial tray, a tibial insert, and a femoral component, may be difficult to align with each other while still maintaining a desired positioning of each component relative to the bone to which it is implanted. In other words, preferred positioning of the femoral component on the femur in order to achieve suitable bone coverage of the femur by the femoral component may not result in the preferred positioning of the femoral component relative to the tibial insert and tibial tray, for example.

By offsetting the location of the dwell point, the position of the femoral component is also shifted relative to the tibial tray medially, laterally, anteriorly, posteriorly, or some combination thereof in order to accommodate different patient needs while still providing desired positioning of the components relative to the patient's anatomy. Illustratively, therefore, the dwell point 50 of the bearing surface 48 of the tibial insert 14 is able to move freely around the axis of rotation 52 such that the dwell point 50 can be centered under the articulating surface of the mating femoral component.

During patient use, the natural or femoral component of the patient's knee rests on the bearing surface 48 of the tibial insert 14 with the most distal end of the femur being received in the dwell point 50. Because the anatomy of each patient is different, the tibial insert 14 will self-adjust for the particular patient to position the dwell point 50 in the correct location to receive the most distal end of the patient's femur. In addition, as the patient moves the knee between flexion and extension, the tibial insert 14 re-adjusts to the patient's needs. Depending on the particular activity being performed by the patient (e.g., playing tennis, walking, running, etc.), the tibial insert 14 will move about the allowable degrees of freedom such that the dwell point 50 is re-positioned to receive the most distal point of the patient's femur. For example, during a particular patient activity, the patient's femur may being to "ride" up on the side of the bearing surface 48 of the tibial insert 14. In response, the tibial insert 14 may rotate or otherwise move such that the dwell point 50 and the most distal end of the patient's femur are again brought into contact. In this way, the tibial insert 14 automatically adjusts position based on the particular anatomy of the patient, as well as, the current activity being performed by the patient.

Additionally, in some embodiments, the movement of the tibial insert 14 may be restricted in one or more directions and/or movements (e.g., rotational or translational movements). For example, as discussed in more detail below in regard to FIGS. 5-8, the tibial insert 14 may be couplable to the tibial tray 12 in one of a limited number of positions. In this way, the dwell point 50 of the tibial insert 14 is postionable in a limited number of locations relative to a fixed reference point. Once so positioned, the tibial insert 14 is allowed to move or otherwise re-position in one or more directions or movements. For example, the tibial insert 14 may be configured to move in a generally anterior-posterior direction, a generally medial-lateral direction, and/or a rotational direction, or the like. Further, each type of movement may be limited in scope. For example, if the tibial insert 14 is allowed to rotate in a particular embodiment, the insert may be restricted to some rotational amount less than 360 degrees in some embodiments. In this way, the motion of the tibial insert 14 may be controlled or otherwise predetermined by the orthopedic surgeon during the performance of the orthopedic surgical procedure. The tibial insert 14 may then perform some amount of "self-adjustment" based on the particular activity performed by the patient.

Figure 4:
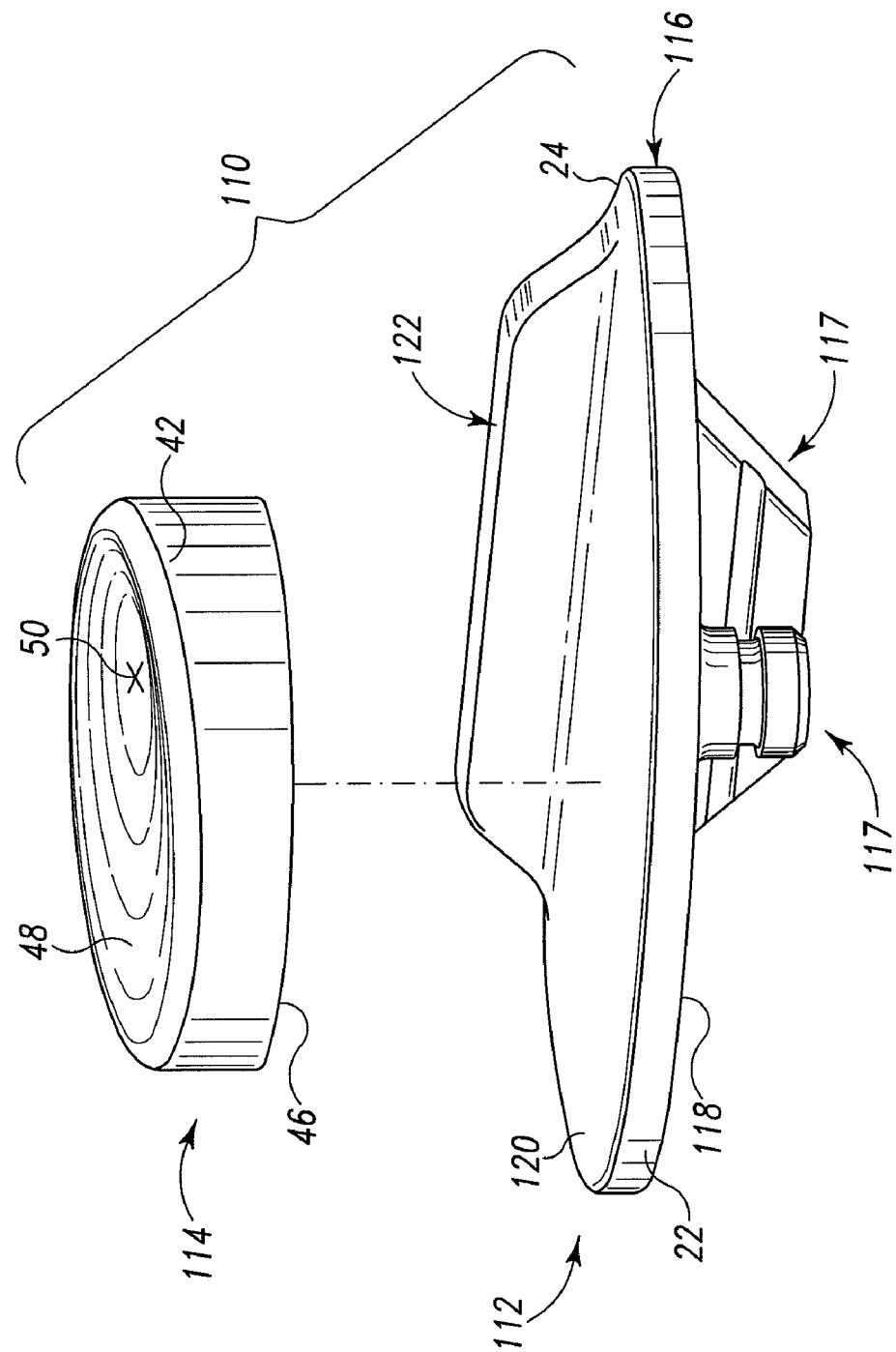
FIG. 4 is an exploded, perspective view of another unicompartmental mobile tibial assembly.

Looking now to FIG. 4 another unicompartmental tibial assembly 110 includes a tibial tray 112 and a tibial insert 114 configured to mate with the tibial tray 112. The tibial tray 112 and the tibial insert 114 are similar to those shown in FIGS. 1-3. As such, like reference numerals are used to denote like components. Illustratively, the tibal tray 112 includes a platform 116 and an anchor 117, such as a keel and peg, extending downwardly from the bottom surface 118 of the platform 116. In use, the keel and peg 117 are coupled to the patient's tibia in order to secure the tibial tray 112 to the tibia. While the illustrative tray 112 includes the keel and peg 117, it is within the scope of this disclosure for the tray 112 to include any suitable anchor for securing the tray 112 to a patient's tibia. The platform 116 includes an upper surface 120 and an end wall 122 extending upwardly from the upper surface 120. Illustratively, the end wall 122 is aligned with the inboard surface 24 of the platform 116 and operates to extend the inboard surface 24 upwardly for placement against a surgically-prepared vertical surface of patient's tibia.

Illustratively, the insert 114 does not include any stem or other component extending downwardly from the bottom surface 46 of the platform 42. Accordingly, the tibial insert 114 is able to move freely on the upper surface 120 of the tray 112. In other words, the movement of the tibial insert 114 relative to the tray 112 is unconstrained such that the insert 114 may move laterally, medially, anteriorly, posteriorly, and may rotate relative to the tray 112. Illustratively, the dwell point 50 of the insert 114 is offset, or spaced-apart, from the center of the generally circular bearing surface 48 of the insert 114, in a similar manner to that which is discussed above in regards to the insert 14 shown in FIGS. 1-3.

Figure 5:
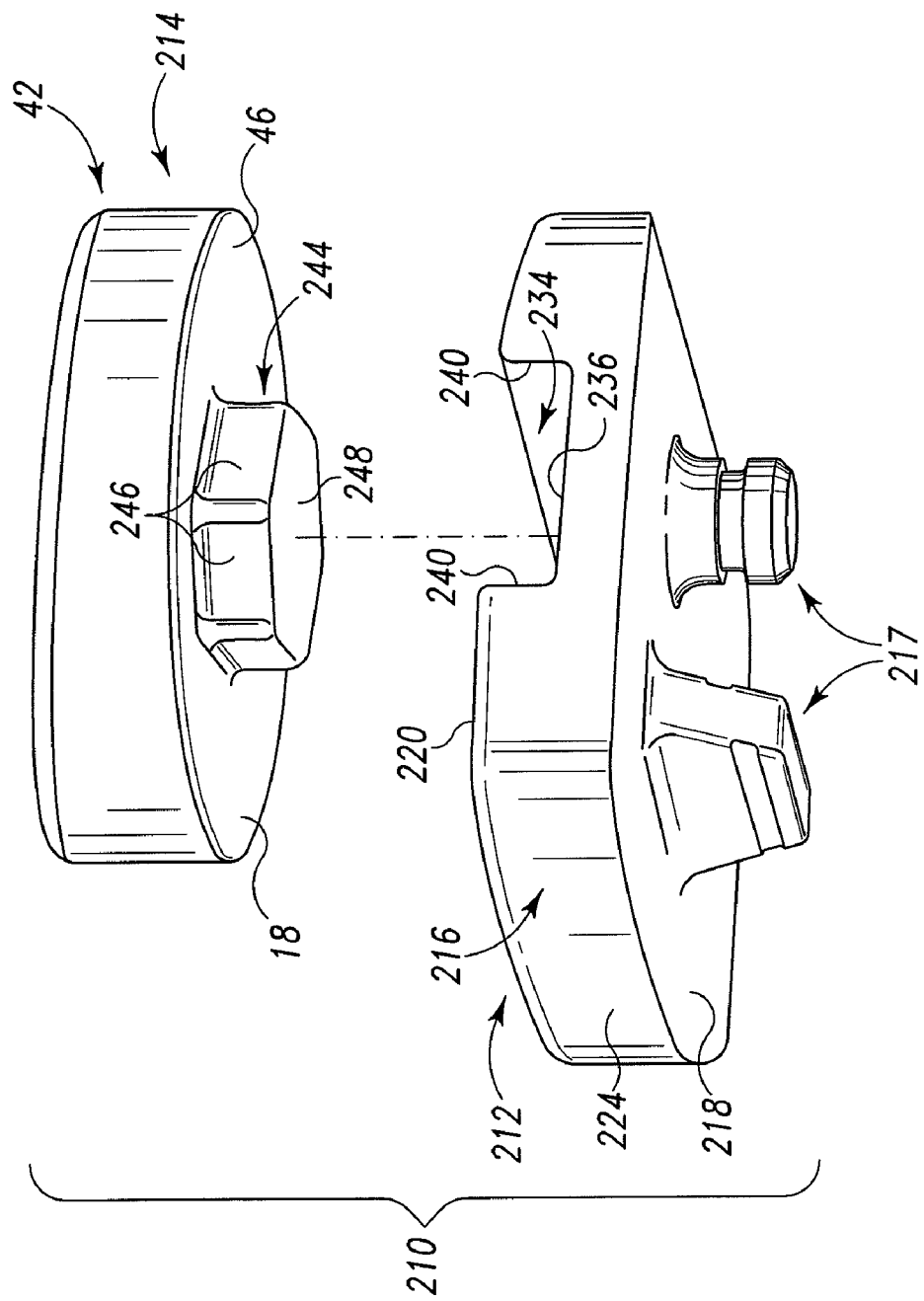
FIG. 5 is an exploded, perspective view of yet another unicompartmental mobile tibial assembly.
Figures 6, 7:
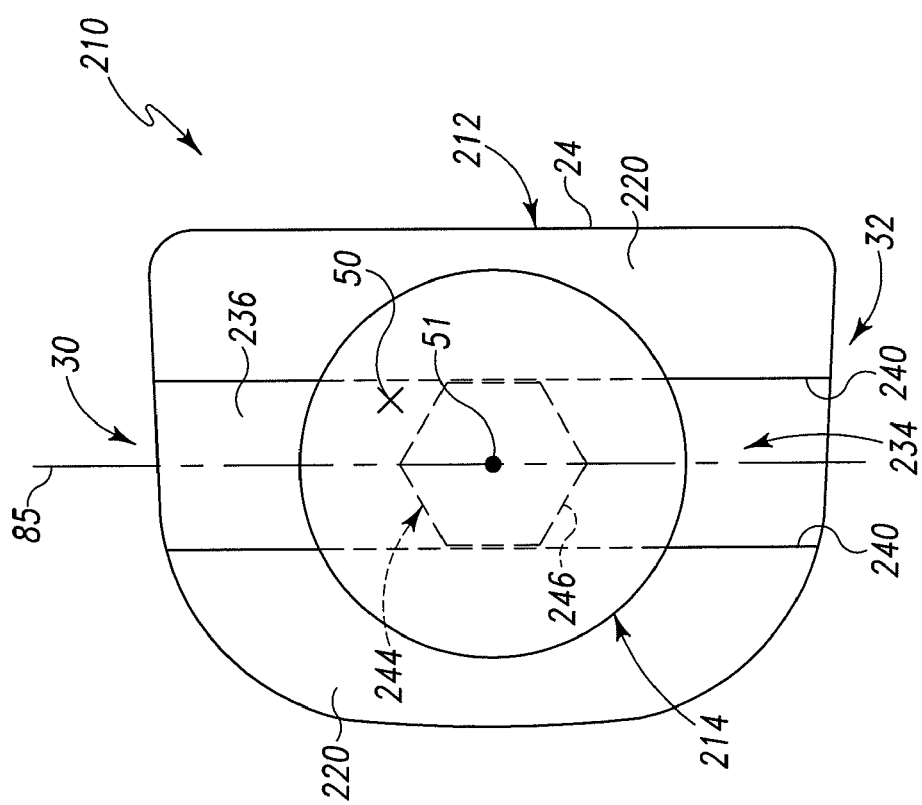
FIGS. 6 and 7 are top views of the tibial assembly of FIG. 5.

Looking now to FIGS. 5-7, a tibial assembly 210 includes a tibial tray 212 and a tibial insert 214 configured to mate with the tibial tray 212. The tibial tray 212 is similar to the tibial tray 12 shown in FIGS. 1-3. As such, like reference numerals are used to denote like components. The tibial tray 212 includes a platform 216 and an anchor 217 (e.g., a keel and a peg) extending downwardly from a bottom surface 218 of the platform 216. A channel 234 is formed in a top surface 220 of the platform 216 to define a bottom wall 236 and generally vertical side walls 240. The channel 234 extends from the anterior side 30 of the platform 216 to the posterior side 32 of the platform 216 and is generally parallel to the inboard surface 224. Similar to the channel 34, The channel 234 is defined in the top surface 220 of the platform 126 in a generally anterior-posterior direction. However, in other embodiments, the channel 234 may be defined in the top surface 220 of the platform 216 in a generally medial-lateral direction, or some combination of a generally anterior-posterior direction and a generally medial-lateral direction (i.e., a generally diagonal direction). Additionally, although the illustrative channel is substantially straight, the tibial tray 212 may include a channel having other configurations in other embodiments. For example, a curved channel may be used in some embodiments. In contrast with the channel 34 of the tray 12 shown in FIGS. 1-3, the channel 234 of the tray 212 does not have an undercut portion for capturing the tibial insert 214. However, it is within the scope of this disclosure for the insert 214 to include a channel having undercut portions.

The tibial insert 214 includes the platform 42 and a stem 244 extending downwardly from the bottom surface 46 of the platform 42. The stem 244 is hexagonal in shape when viewed in a bottom plan view. Accordingly, the stem 244 includes six side walls 246 as well as a bottom wall 248.

In use, the stem 244 of the insert 214 is placed within the channel 234 of the tray 212 such that the bottom surface 46 of the insert 214 rests on the top surface 220 of the platform 216 of the tray 212. The stem 244 is able to slide within the channel 234 relative to the tray 212 in the anterior and posterior directions. As shown in FIG. 6, opposite or parallel side walls 246 of the stem 244 are each adjacent one of the side walls 240 defining the channel 234. Illustratively, the stem 244 may be placed within the channel 234 in six different positions in order to change the orientation of the insert 214, and the dwell point 50 of the insert, relative to the tray 212.

Accordingly, the insert 214 may be oriented in an initial position, as shown in FIG. 6, such that one of the pairs of parallel side walls 246 is adjacent the side walls 240 of the channel 234. Such a placement orients the dwell point 50 of the insert in the position (relative to the tray 212) shown in FIG. 6. The insert 214 may be repositioned relative to the tray 212 by removing the stem 244 from the channel 234 and rotating the insert 214 such that a different pair of parallel side walls 246 are adjacent the side walls 240 of the channel 234. For example, as shown in FIG. 7, the tibial insert 214 has been rotated approximately 60 degrees in a counter clockwise direction in order to orient the dwell point 50 of the insert 212 in the position (relative to the tray 212) shown in FIG. 7. Accordingly, the dwell point 50 of the insert 214 may be positioned by the surgeon in one of six orientations relative to the tray 212 depending upon the particular anatomy and/or activity needs of the patient.

Illustratively, the insert 214 is not rotatable relative to the tray 212, but is able to translate within the channel 234 in the anterior and posterior directions. Further, as noted above, the dwell point 50 of the insert 214 is spaced-apart from the center 51 of the bearing surface 48 of the insert 214. Similarly, the dwell point 50 of the insert 214 is spaced-apart from the midpoint of the width, or centerline 85, of the channel 234, as discussed above in regards to the tibial insert 14.

While the tibial assembly 210 is a mobile tibial assembly, it is also within the scope of this disclosure to provide a fixed tibial assembly including a tibial insert having an offset dwell point that my be oriented relative to the tibial tray in a number of fixed positions. In other words, the tibial tray may be provided with a recess such as the channel 234 shown (to allow the stem 244 to translate relative to the tray) or a bore shaped similarly to the shape of the stem 244, for example, in order to receive the stem 244 in a fixed position therein. Further, while the illustrative tibial insert 214 is able to be oriented in six different positions relative to the tray 212, it is within the scope of this disclosure to provide a tibial insert that is able to be oriented in any number of positions relative to the tray in order to position the dwell point in any suitable location relative to the tray. For example, the stem of the tibial insert may be octagonal to permit the tibial insert to be oriented in eight different positions relative to the tibial tray.

Figure 8:
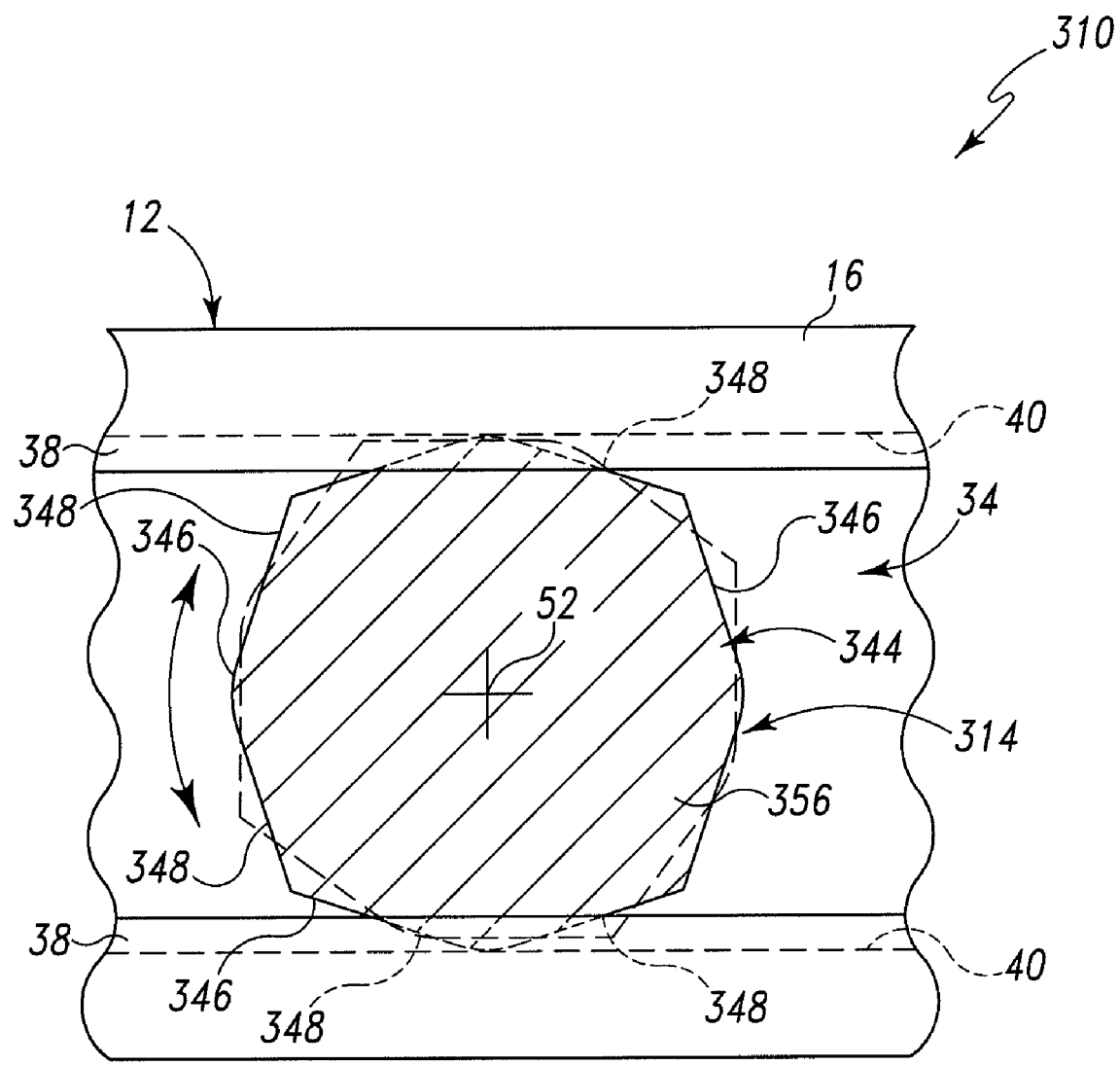
FIG. 8 is a sectional view of another tibial assembly.

Looking now to FIG. 8, a portion of another tibial assembly 310 is shown. The assembly 310 includes the tibial tray 12 shown in FIGS. 1 and 2 and, as such, the channel 34 of the platform 16 includes overhang portions 38 and undercut portions 40. The assembly 310 further includes a tibial insert having a stem 344 including a narrow neck portion (not shown) and a wider base portion 356 similar to that of the stem 44 of the tibial tray 12. Illustratively, the base portion 356 of the stem 344 includes four curved side walls 346 such that each side wall 346 includes two wall portions 348. The base portion 356 of the stem 344 is received within the channel 34 such that the curved side walls 346 are received within the undercut portions 40 of the channel 34.

The four side walls 346 of the stem 344 allow the surgeon to orient the tibial insert 314 in four different positions relative to the tray 12 in order to position the dwell point of the tray 12 to suit the individual needs of the patient. Further, the curved side walls 346 permit limited rotation of the stem 344 relative to the tray 12 about the axis of rotation 52, as shown in phantom in FIG. 8. Additionally, the width of the base of the stem 344 may be slightly smaller than a width of the channel 34 in order to further permit limited rotation of the stem 344 relative to the tray 12. In other words, the rounded portions of the curved side walls 346 are able to move past the inner wall of the channel 34 defining the undercut portions 40 as the stem 344 is rotated relative to the tray 12 whereas the corners between each side wall 346 act as a stop and engage the inner wall of the channel 34 once the stem 344 has been rotated to a particular degree to prevent the stem 344 from rotating further. Illustratively, the stem 344 is able to rotate approximately 10 degrees about the axis of rotation 52 in either direction. However, it is within the scope of this disclosure to include a tibial assembly in which the tibial insert is able to rotate (in a limited manner, i.e., less than 360 degrees of rotation) relative to the tibial tray through any suitable degrees of rotation. Furthermore, while the stem 344 of the tibial insert 314 includes four curved side walls, it is within the scope of this disclosure to include a stem having any number of curved and/or straight side walls.

Various tibial assemblies 10, 110, 210, 310 are disclosed herein. Each tibial assembly includes a tibial tray and a tibial insert configured to rest on the tibial tray. Illustratively, while the tibial assemblies 10, 110, 210, 310 are mobile tibial assemblies (i.e., the tibial insert is able to move relative to the tibial tray), it is within the scope of this disclosure to include fixed tibial assemblies (i.e., the tibial insert is not able to move relative to the tibial tray) having one or more features or characteristics disclosed herein with respect to the tibial assemblies 10, 110, 210, 310.

Illustratively, the tibial assemblies 10, 110, 210, 310 disclosed herein each include a tibial insert having a dwell point 50 which is offset from one or more of the following: (1) the axis of rotation of the tibial insert relative to the tibial tray; (2) the center of the bearing surface; and (3) the centerline or midpoint of the width of any channel or other feature of the tibial tray which operates to capture or constrain movement of the tibial insert relative thereto.

Each tibial insert of the various tibial assemblies disclosed herein may be made by determining a center of a bearing surface of the tibial insert when the tibial insert is viewed in a plan view and determining an offset location on the bearing surface to locate the dwell point of the bearing surface. The offset location is spaced-apart from the center of the bearing surface. Further, the tibial insert may be fabricated such that dwell point of the bearing surface is located at the offset location. Illustratively, as discussed above, the offset location may be spaced 2-8 mm apart from the center of the bearing surface or, in some embodiments, may be spaced 3-6 mm apart from the center of the bearing surface.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. A mobile tibial assembly comprising:
a tibial tray configured to be coupled to a surgically-prepared surface of the proximal end of a tibia, the tibial tray including a platform having an upper surface and a channel extending along a longitudinal axis, the channel being formed in the upper surface to define spaced-apart first and second side walls and a bottom surface therebetween having a width extending transverse to the longitudinal axis, and
a unicompartmental tibial insert including a platform and a stem extending downwardly from the platform and received within the channel of the tibial tray, the platform including (i) a bottom surface configured to engage the upper surface of the platform of the tibial tray and (ii) a generally circular upper bearing surface having a center and defining a dwell point offset from the center,
wherein (i) the center of the upper bearing surface and a midpoint of the width of the bottom surface of the channel lie on the longitudinal axis of the channel, and (ii) the dwell point of the tibial insert is spaced-apart from the midpoint of the width of the bottom surface of the channel in the medial/lateral direction.

2. The mobile tibial assembly of claim 1, wherein the dwell point is laterally spaced 2-8 mm apart from the midpoint of the width of the bottom surface of the channel.

3. The mobile tibial assembly of claim 2, wherein the dwell point is laterally spaced 3-6 mm apart from the midpoint of the width of the bottom surface of the channel.

4. The mobile tibial assembly of claim 1, wherein the stem of the tibial insert is generally circular when viewed in a bottom plan view.

5. The mobile tibial assembly of claim 1, wherein the stem of the tibial insert is generally hexagonal when viewed in a bottom plan view.

6. The mobile tibial assembly of claim 5, wherein the stem of the tibial insert is configured to be oriented in six different positions within the channel of the tibial tray.

7. The mobile tibial assembly of claim 5, wherein the tibial insert is oriented in a first position relative to the tibial tray such that a first side wall of the stem of the tibial insert is engaged with the first side wall of the channel and a second side wall of the stem of the tibial insert is engage with the second side wall of the channel.

8. The mobile tibial assembly of claim 7, wherein the tibial insert is oriented in a second position relative to the tibial tray such that a third side wall of the stem of the tibial insert is engaged with the first side wall of the channel and a fourth side wall of the stem of the tibial insert is engaged with the second side wall of the channel.

9. The mobile tibial assembly of claim 8, wherein the tibial insert is oriented in a third position relative to the tibial tray such that a fifth side wall of the stem of the tibial insert is engaged with the first side wall of the channel and a sixth side wall of the stem of the tibial insert is engaged with the second side wall of the channel.

10. The mobile tibial assembly of claim 1, wherein the stem of the tibial insert includes four side walls.

11. The mobile tibial assembly of claim 10, wherein the side walls are each curved.

12. The mobile tibial assembly of claim 1, wherein the channel extends from an anterior end of the platform of the tibial tray to a posterior end of the platform of the tibial tray.

13. A unicompartmental mobile tibial assembly comprising:
a tibial tray configured to be coupled to a surgically-prepared surface of the proximal end of a tibia, the tibial tray including a platform having an upper surface and a channel formed in the upper surface to define spaced-apart first and second side walls and a bottom surface therebetween, and
a tibial insert including a platform and a stem having four side walls that extends downwardly from the platform and is received within the channel of the tibial tray, the platform including (i) a bottom surface configured to engage the upper surface of the platform of the tibial tray and (ii) an upper bearing surface defining a dwell point,
wherein (i) the dwell point of the tibial insert is spaced-apart from a midpoint of the width of the bottom surface of the channel in the medial/lateral direction, and the tibial insert is configured to rotate relative to the tibial tray approximately 20 degrees.

14. A mobile tibial assembly comprising:
a tibial tray configured to be coupled to a surgically-prepared surface of the proximal end of a patient's tibia, the tibial tray having a platform including an upper surface, and a unicompartmental tibial insert including a platform having (i) a bottom surface positioned on the upper surface of the tibial tray and (ii) an upper bearing surface, wherein a dwell point of the upper bearing surface is spaced-apart 2-8 mm from an axis of rotation about which the tibial insert rotates relative to the tibial tray when the tibial insert is positioned on the tibial tray.

15. The mobile tibial assembly of claim 14, wherein the tibial insert is configured to rotate relative to the tibial tray approximately 360 degrees about the axis of rotation.

16. The mobile tibial assembly of claim 14, wherein the tibial insert is configured to rotate relative to the tibial tray approximately 20 degrees about the axis of rotation.

17. The mobile tibial assembly of claim 14, wherein the platform of the tibial insert is generally circular in shape when viewed in a plan view.

\* \* \* \* \*